United States Patent [19]

Chen et al.

[11] Patent Number: 4,844,071
[45] Date of Patent: Jul. 4, 1989

[54] ENDOSCOPE COUPLER DEVICE

[75] Inventors: Chingfa Chen, Irvine; Danny L. Pastrick, Fountain Valley, both of Calif.

[73] Assignee: Baxter Travenol Laboratories, Inc., Deerfield, Ill.

[21] Appl. No.: 175,937

[22] Filed: Mar. 31, 1988

[51] Int. Cl.[4] ............................................. A61B 1/00
[52] U.S. Cl. ............................................ 128/6; 128/4
[58] Field of Search ................. 128/3, 4, 5, 6, 7, 8; 604/905

[56] References Cited

U.S. PATENT DOCUMENTS

| | | | |
|---|---|---|---|
| 4,196,990 | 4/1980 | Forsyth | 128/6 X |
| 4,277,168 | 7/1981 | Oku | 128/4 X |
| 4,310,228 | 1/1982 | Terada | 128/6 X |
| 4,323,304 | 4/1982 | Ishii | 128/6 |
| 4,407,272 | 10/1983 | Yamaguchi | 128/6 |
| 4,413,278 | 11/1983 | Feinbloom | 358/98 X |
| 4,439,030 | 3/1984 | Ueda | 128/4 X |
| 4,440,157 | 4/1984 | Shishido | 128/6 |
| 4,478,212 | 10/1984 | Asano | 128/6 |
| 4,487,489 | 12/1984 | Takamatsu | 128/6 X |
| 4,539,587 | 9/1985 | Danna et al. | 128/6 X |
| 4,552,131 | 11/1985 | Omagari | 128/6 |
| 4,565,423 | 1/1986 | Ueda | 128/6 X |
| 4,600,938 | 7/1986 | Sluyter et al. | 358/98 |
| 4,600,939 | 7/1986 | Sluyter et al. | 358/98 |
| 4,600,940 | 7/1986 | Sluyter | 358/98 |
| 4,601,284 | 7/1986 | Arakawa et al. | 128/6 |
| 4,604,992 | 8/1986 | Sato | 128/6 |
| 4,611,888 | 9/1986 | Prenovitz et al. | 128/6 X |
| 4,624,243 | 11/1986 | Lowery et al. | 128/6 |
| 4,639,772 | 1/1987 | Sluyter et al. | 358/98 |
| 4,646,724 | 3/1987 | Sato et al. | 128/6 |
| 4,667,230 | 5/1987 | Arakawa et al. | 358/98 |
| 4,667,656 | 5/1987 | Yabe . | |
| 4,736,733 | 4/1988 | Adair | 128/6 |
| 4,756,304 | 7/1988 | Watanabe | 128/6 |

Primary Examiner—William H. Grieb
Attorney, Agent, or Firm—Gordon L. Peterson; Loyal M. Hanson

[57] ABSTRACT

A coupler device for coupling an endoscope to a camera head includes a housing that defines an enclosed light path extending along an optical axis between first and second end portions of the housing together with mounting components for attaching the first end portion of the housing to an endoscope and the second end portion of the housing to a camera head so that the light path extends toward the camera head. A single lens mounted within the housing intermediate the first and second end portions magnifies an image from the endoscope in order to provide a magnified image to the camera head, the lens being a single refracting optical element for magnifying the image from the endoscope that is the sole refracting optical element for magnifying the image. A quick-release arrangement in one embodiment enables attachment of the endoscope by advancing the endoscope axially without having to rotate it while a focusing ring enables fine focusing adjustments. An imaging system includes an imaging endoscope with a quick-release connector hub, a coupler device for attachment between the connector hub and a camera head, and an interchangeable eyepiece for interfacing the endoscope to a human eye.

29 Claims, 3 Drawing Sheets

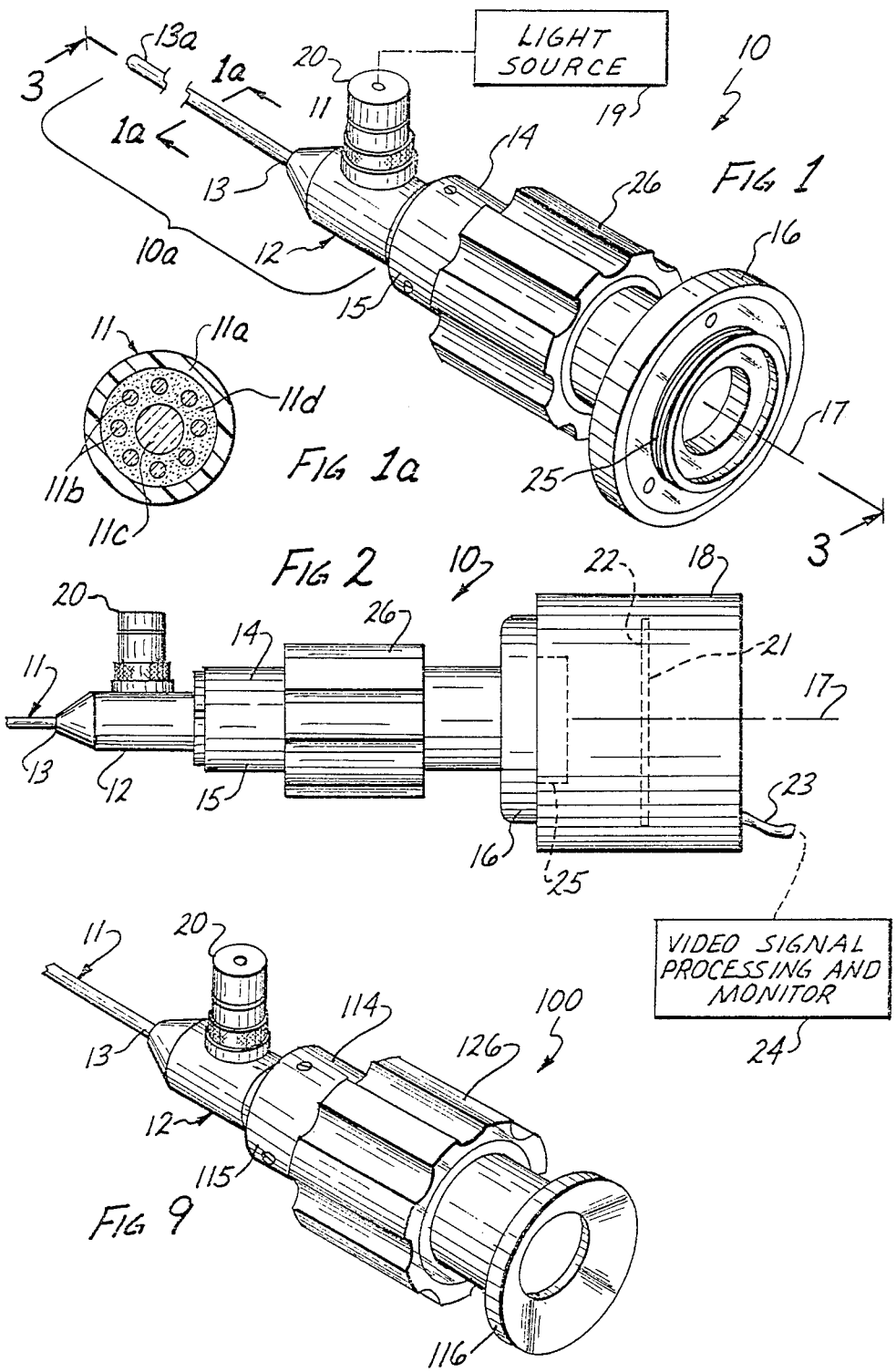

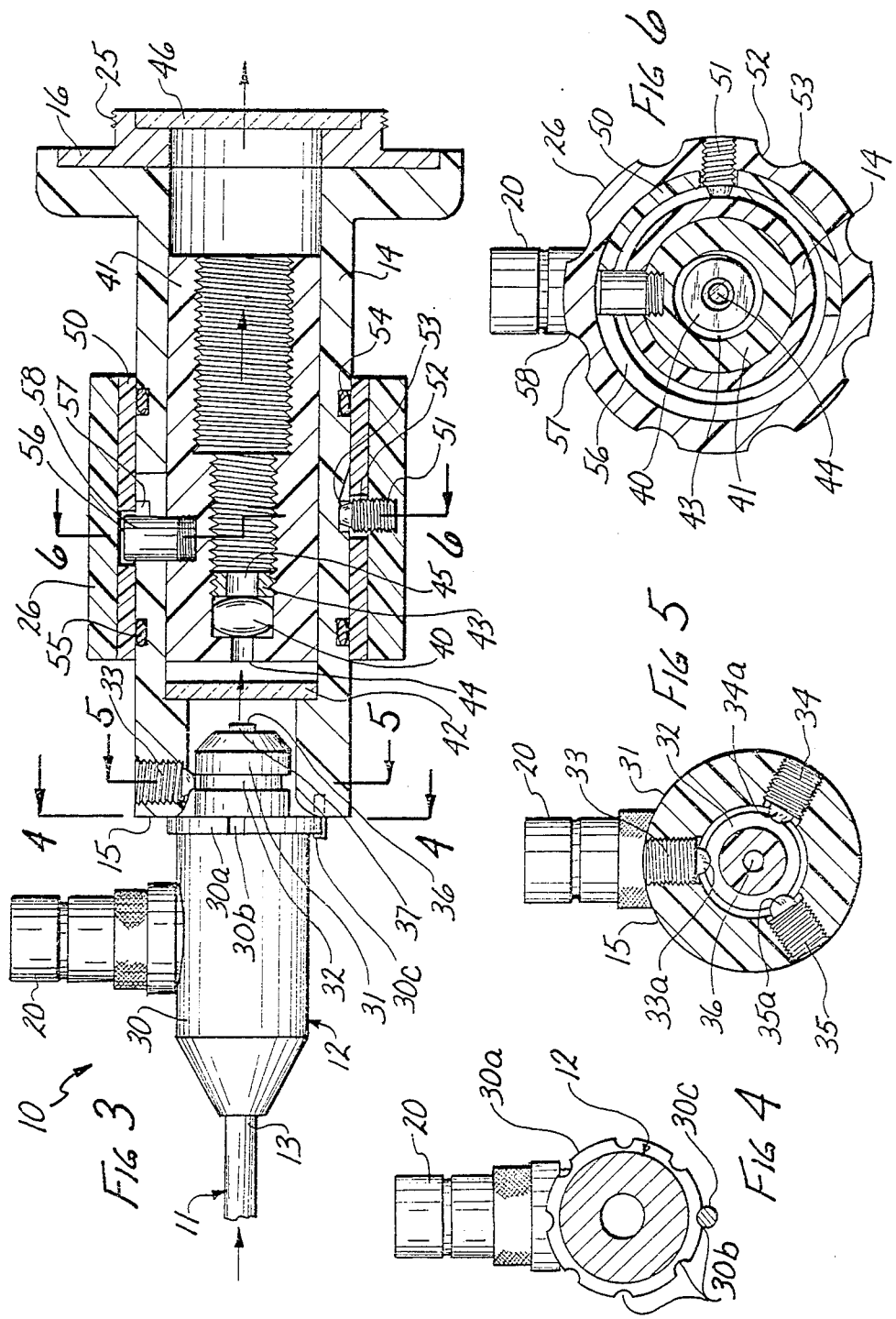

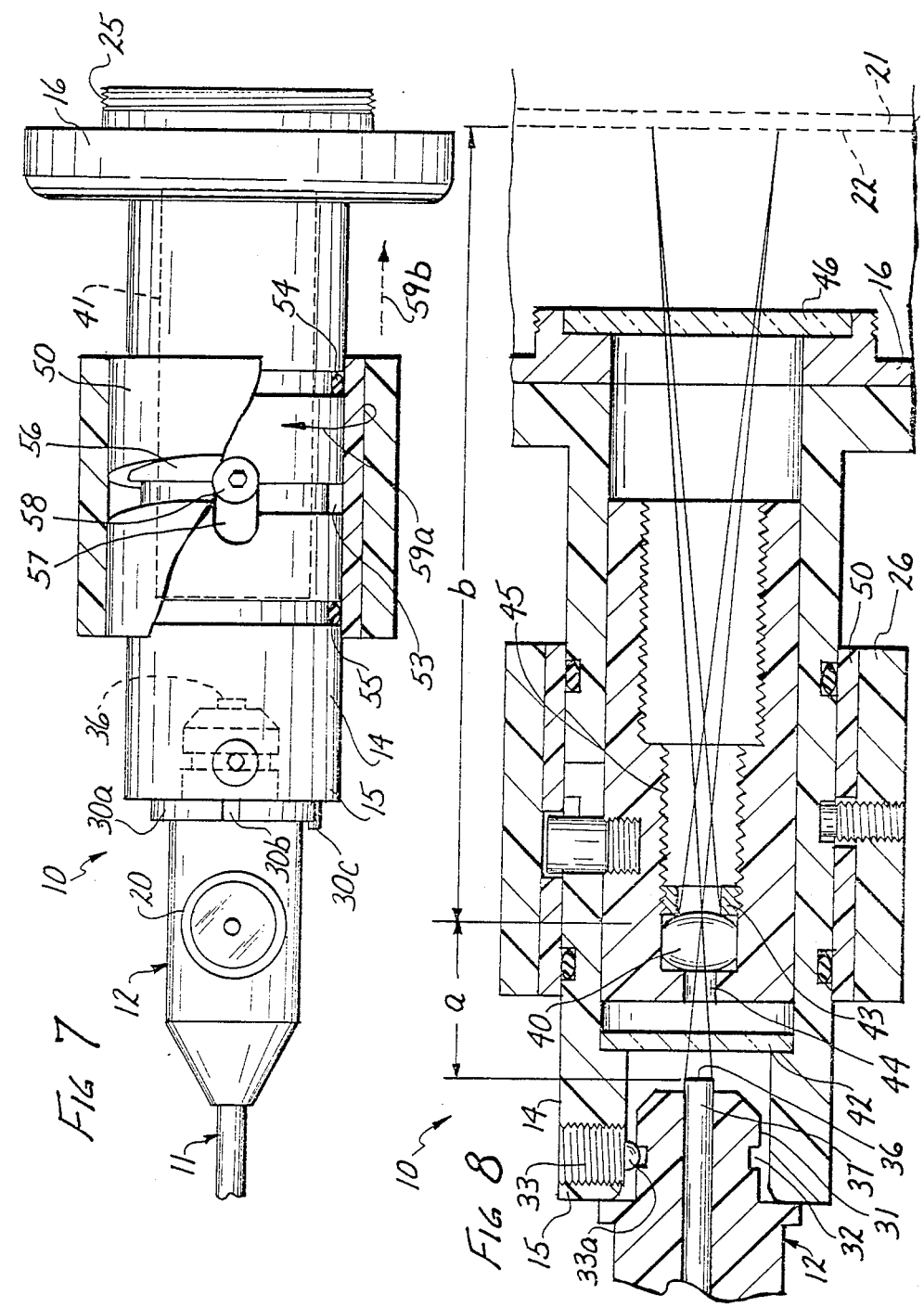

ENDOSCOPE COUPLER DEVICE

BACKGROUND OF THE INVENTION

1. Technical Field

This invention relates generally to endoscopes, and more particularly to an endoscope coupler device for coupling an endoscope to a camera.

2. Background Information

An endoscope may include an elongated section that contains an imaging fiber surrounded by a bundle of illuminating fibers. The physician advances the elongated section within a body until the distal end is proximate a region of interest. Then, illuminating light introduced at the proximal end propagates along the illuminating fibers to illuminate the region of interest, with reflected light propagating back along the imaging fiber for viewing.

A connection hub attached to the proximal end interfaces the optical fibers to supporting components, coupling a separate source of illuminating light to the illuminating fibers and an eyepiece to the imaging fiber. The eyepiece attaches to the connection hub as an interface between the imaging fiber and the user's eye. It provides a visually discernible image of the region of interest, and the user simply looks into the eyepiece with one eye to view the image.

One such endoscope is described in U.S. Pat. No. 4,624,243 to Lowery at al. entitled "Endoscope Having A Reuseable Eyepiece And A Disposable Distal Section." An objective lens and a plano lens mounted within the eyepiece combine to present the image at a viewing port, and the user rotates the eyepiece housing slightly to bring the image into focus.

However, it may be desirable to record the image with such imaging equipment as a video camera. This is sometimes accomplished by utilizing a special adapter having one end that clamps onto the eyepiece over the viewing port and another end that screws onto a remote video camera head. Lenses within the adapter pass the image to the plane of a camera sensor chip within the camera head and this adapts the eyepiece to the camera head.

Although such an adapter may be effective in many respects, there are certain problems that need to be overcome. For example, using the combination of an eyepiece and an adapter involves the relative expense and complexity of two separate devices. This may include interrelated focusing adjustments of two lens systems, an undesirably large adapter size for a desired image size, and extra time and inconvenience for mounting and use. In addition, the surface reflections and limited numerical aperture of multiple optical elements decrease light intensity.

Consequently, it is desirable to have a new and improved endoscope coupler device that alleviates these concerns. In this regard, it is particularly desirable to have the coupler device produce an image of greater intensity and sufficient size to cover a substantial portion of a conventional camera sensor chip.

SUMMARY OF THE INVENTION

This invention solves the problems outlined above by providing a dedicated endoscope coupler device that includes a single refracting optical element or lens within a single mounting component or housing. One end of the housing mounts on the connector hub and the other mounts directly on the camera head.

This arrangement results in less expense and complexity. It simplifies mounting. It eliminates multiple focusing adjustments, and it increases light intensity while decreasing component size of the endoscope to camera coupling arrangement. In addition, one lens mounted within one housing facilitates fabrication of different couplers having different magnification, this being done by changing physical dimensions of the housing instead of optical characteristics of the lens.

Generally, a coupler device constructed according to the invention includes a housing defining an enclosed light path that extends along an optical axis between first and second end portions of the housing. This can be a cylindrically shaped component about seven or eight centimeters long and about two centimeters in diameter, for example.

According to one aspect of the invention, a first mounting arrangement is provided on the first end portion of the housing for attaching the first end portion to an endoscope, and a second mounting arrangement is provided on the second end portion for attaching the second end portion to a camera head so that the light path extends toward the camera head. Thus, the housing can be mounted to extend directly between a connector hub on the endoscope and a remote video camera head, for example, as a dedicated coupler device.

According to another aspect of the invention, there is provided a single refracting optical element or lens mounted within the housing intermediate the first and second end portions for magnifying an image from the endoscope in order to provide a magnified image to the camera head. This is the sole refracting optical element for magnifying the image, and its position may be adjustable for focusing purposes.

According to yet another aspect of the invention, there is provided an an endoscope assembly that includes a quick-release connector hub. This enables a user to attach the connector hub to and detach the connector hub from the first end portion of the housing by advancing the connector hub axially relative to the first end portion of the housing without having to rotate the connector hub.

In line with the above, an imaging system constructed according to the invention includes an imaging endoscope with a quick-release connector hub, a coupler device for attachment between the connector hub and a camera head, and an interchangeable eyepiece. This enables use of either the eyepiece or coupler device by snapping off one and snapping on the other. The eyepiece may include a single lens and focusing components similar to those of the coupler device for the cost benefits of component standardization.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a perspective view of a coupler device constructed according to the invention shown attached to an endoscope;

FIG. 1a is an enlarged cross sectional view taken on line 1a—1a of FIG. 1 illustrating internal details of the endoscope;

FIG. 2 is a diagrammatic view of the coupler device operationally connected between the endoscope and a camera head;

FIG. 3 is an enlarged cross sectional view of the coupler device taken on line 3—3 of FIG. 1;

FIG. 4 is a cross sectional view of the coupler device taken on line 4—4 of FIG. 3;

FIG. 5 is a cross sectional view taken on line 5—5 of FIG. 3;

FIG. 6 is a cross sectional view taken on line 6—6 of FIG. 3;

FIG. 7 is a top view of the coupler device showing operation of the focusing components;

FIG. 8 is a further enlarged cross sectional view showing optical details of the coupler device; and FIG. 9 is a perspective view of a compatible eyepiece.

DESCRIPTION OF THE PREFERRED EMBODIMENTS

Referring now to FIG. 1, there is shown a coupler device 10 constructed according to the invention that is mounted on an endoscope assembly 10a. This endoscope assembly 10a includes an endoscope 11 having a proximal end portion 13 and a distal end portion 13a, and a connector hub 12 attached to the proximal end portion 13.

The device 10 includes a housing 14 composed of a suitable rigid material, such as a black anodized aluminium alloy, that extends between a first end portion 15 and a second end portion 16. It is of unitary construction in the sense that it does not include an eyepiece type of component adapted for use with a camera head. The illustrated housing 14 is is cylindrically shaped with a hollow interior that defines an enclosed light path extending along an optical axis 17 (FIG. 1) between the first and second end portions 15 and 16.

As an idea of size, the housing 14 is approximately six to seven centimeters long and about three to four centimeters in diameter at the first end portion 15. As will become apparent, various other shapes and sizes may be employed according to the precise application without departing from the inventive concepts disclosed.

The first end portion 15 of the housing 14 cooperates with the connector hub 12 to serve as first mounting means for attaching the first end portion 15 of the housing 14 to the endoscope 11. In addition, the second end portion 16 is suitably configured to serve as second mounting means for attaching the second end portion 16 of the housing 14 to a camera head 18 (FIG. 2) so that the light path extends toward the camera head 18.

So attached, the device 10 couples the endoscope assembly 10a and thereby the endoscope 11 to the camera head 18 for purposes of recording images provided by the endoscope 11, and in so doing it retains the connector hub 12 at a fixed distance from the camera head 18. In other words, this arrangement may be said to serve as camera coupler means for coupling the endoscope 11 directly to the camera head 18.

In this regard, the invention concerns those endoscopes that contain an imaging fiber and at least one illuminating fiber—typically a bundle of illuminating fibers surrounding an imaging fiber. As used herein, the word endoscope refers to such an endoscope, which may also be called an imaging endoscope.

Fiber placement within the flexible endoscope 11 is shown in FIG. 1a. The endoscope 11 includes a flexible outer tube 11a in which a bundle of illumination fibers 11b and an imaging fiber 11c are retained by a suitable flexible potting compound 11d. The illumination fibers 11b and the imaging fiber 11c extend between the proximal end portion 13 and the distal end portion 13a. The illumination fibers 11b serve as illumination means for transmitting light from the proximal end portion 13 to the distal end portion 13a, and the imaging fiber 11c serves as means for transmitting an image from the distal end portion 13a to the proximal end portion 13.

The endoscope 11 is similar in many respects to the imaging endoscope described in U.S. Pat. No. 4,624,243 to Lowery at al. entitled "Endoscope Having A Reuseable Eyepiece And A Disposable Distal Section." This patent is incorporated herein for the details of construction provided.

The physician advances the endoscope 11 within the body of a patient until the endoscope reaches a region of interest. Then, illuminating light introduced through a coupling structure 20 on the connection hub 12 enters the proximal end portion 13 of the endoscope 11 and propagates along illuminating fibers to illuminate the region of interest, with reflected light propagating back along an imaging fiber for viewing.

The connection hub 12 interfaces the optical fibers to supporting components for this purpose. It includes the coupling structure 20 (FIGS. 1 and 2) with which a separate source of illuminating light or light source 19 (FIG. 1) is coupled to illuminating fibers within the endoscope 11, the coupling structure 20 preferably being configured to mate with conventional light conducting components. In addition, the connection hub 12 is configured for attachment to the housing 14 in order to couple an imaging fiber within the endoscope 11 to the coupler device 10 and thereby to the camera head 18 (FIG. 2).

The camera head 18 represents a conventional remote video camera head, such as that manufactured by Medical Dynamics. It includes a sensor chip 21, such as the one-half inch chip manufactured by Panasonic. An image from the endoscope 11 passes through the device 10 to the camera head 18 and onto the forward surface 22 of the sensor chip 21. There, the sensor chip 21 conventionally produces an electrical signal that is transmitted over a cable 23 to other video components that include a video monitor 24 (FIG. 2).

The camera head 18 includes a conventional C-mount (not illustrated) that can be used for attachment of such components as a lens system, and the second end portion 16 of the housing 14 is configured for attachment to the C-mount. In other words, the second end portion 16 includes a threaded portion 25 (FIG. 1) that is dimensioned and arranged (about three and one-half centimeters in diameter) so that it can be screwed onto the camera head 18 (FIG. 2).

Of course, the inventive concepts disclosed include the use of other mounting arrangements instead, such as a bayonet type mounting for attachment to a camera head using that type of mounting arrangement. To facilitate adaptation of the device 10, the second end portion 16 may be flanged and the threaded portion 25 may be configured as a seprate component that can be mounted by suitable means such as screws on the flanged second end portion 16. This enables the manufacturer and user to attach a bayonet-type component to the housing 14 instead of the threaded portion 25.

To use the device 10 with the endoscope assembly 10a, the user screws the threaded portion 25 of the second end portion 16 onto the camera head 18. Next, the user advances the connector hub 12 and first end portion 15 of the housing 14 axially toward each other until they snap together as subsequently discussed.

Then, with the light source 19 coupled to the coupling structure 20 and the distal end portion 13A of the endoscope 11 advanced to a region of interest, the user views an image of the region of interest by viewing a display on the screen of the video monitor 24. As the display is viewed, the user rotates a focusing ring 26 on the device 10 (FIGS. 1 and 2) in order to focus the image on the forward surface 22 of the sensor chip 21 and thereby to focus the display on the monitor screen. In other words, the focusing ring 26 is a ring circumscribing the housing 14 that is mounted on the housing 14 enable a user to rotate the ring about the optical axis 17. When operational procedures are completed, the device 10 is detached from the connector hub 12 and the camera head 18 and sterilized or otherwise prepared for later reuse.

Further details of the device 10 and the endoscope assembly 10a are shown in the enlarged views of FIGS. 3-8. The connector hub 12 includes a hub housing 30 that extends to a tip portion 31 (FIG. 3). The tip portion 31 is dimensioned and arranged to fit within the first end portion 15 of the housing 14 as illustrated. A circularly shaped flange portion 30a of the hub housing 30 (FIG. 4) defines a plurality of notches 30b in its outer periphery that are located at spaced apart locations (FIGS. 3 and 4).

When the the tip portion 31 is inserted into the end portion 15, the user aligns a pin 30c that extends from the end portion 15 with one of the notches 30b. So disposed, the pin 30c engages the flange portion 30a to prevent rotation of the hub housing 30 relative to the end portion 15. In other words, this arrangement holds the endoscope assembly 10a in a fixed angular relationship relative to the device 10. Thus, this arrangement serves as antirotation means for preventing rotation of the end portion 15 relative to the connector hub 12. The pin 30c is attached by suitable means, such as a press fit within a hole in the end portion 15, but other means for preventing rotation may be employed.

The tip portion 31 includes a recess in the form of a circumferentially entending groove 32 into which a radially extending member of screw 33 extends (FIG. 3) as well as radially extending members or screws 34 and 35 (FIG. 5). The screws 33-35 combine with the tip portion 31 to serve as means for retaining the first end portion 15 of the housing 14 adjacent the proximal end 36 of an endoscope imaging fiber 37 (FIGS. 3 and 5).

This is done so that the proximal end 36 of the endoscope imaging fiber 37 faces into the housing 15 along the light path as depicted by the arrows point to the right of the sheet of drawings in FIG. 3. It should be understood in this regard that the size of the imaging fiber 37 is exaggerated in the drawings for illustrative convenience. Although another form of recess may be employed within certain inventive concepts, the groove 32 permits relative rotation between the endoscope assembly 10A and the device 10.

Each of the screws can be adjusted to obtain the desired concentric relationship between the tip portion 31 and the housing 14. This facilitates alignment of the proximal end 36 of the imaging fiber 37 and the housing 14 without having to maintain severe dimensional tolerances during the fabrication of the housing 14 and connector hub 12. This in turn facilitates alignment of the proximal end 36 with optical components within the housing 14 that are subsequently described.

In addition, each of the screws has a spring loaded ball arrangement configured according to known techniques to engage the forward tip portion 31 by extending into the groove 32. These are the balls 33A, 34A, and 35A in FIG. 5, and they bear radially inward toward the forward tip portion 31 under influence of suitable known spring biasing means within each screw that enables the ball to move radially outwardly as the tip portion 31 is inserted into the end portion 15 and then move back into the groove 32. This movement of the balls 33A, 34A, and 35A also occurs as the tip portion 31 is withdrawn from the end portion 15.

Thus, this spring loaded ball arrangement combines with the groove 32 to serve as quick-release means for enabling a user to attach the connector hub 12 to and detach the connector hub 12 from the first end portion 15 of the housiing 14 by advancing the connector hub 12 and the first end portion 15 axially toward each other until they snap into engagement. This can be done without having to rotate the connector hub 12 as would be required with a screw-on arrangement.

From another viewpoint, this arrangement serves as means for maintaining concentricity between the tip portion 31 and the first end portion 15 without having to maintain the dimensional tolerances that might otherwise be required. Maintaining concentricity is important in order to maintain the proximal end 36 of the optical fiber 37 aligned with an optical element or lens 40 mounted within the housing 14. The lens 40 may be an eight millimeter lens, for example, that is configured according to known optical design techniques to magnify an image provided by the endoscope adjacent the proximal end 36 of the optical fiber 37 in order to thereby provide a magnified image to the sensor chip that covers a substantial portion of the chip, sixty percent or more, for example.

Radially extending members other than the screws 33-34 may be used within the broader inventive concepts disclosed to maintain concentricity and enable quick release. For example, the end portion 15 can be configured so that it defines an annular groove facing the groove 32 in FIG. 3, and a spring clip provided that fits in the annular groove (not shown). In such an arrangement, the spring clip is shaped so that portions of it extend toward and into the groove 32 to engage the tip portion 31. These portions are also radially extending members. The spring clip deforms resiliently so that these radially extending members move radially, as do the balls 33A, 33B, and 33C, and this enables placement and removal of the connector hub 12.

The lens 40 is the only refracting optical element in the device 10 in the sense that it is a single unit, including, for example, a singlet or a doublet lens configuration, but not including an arrangement of separated elements. It serves as single lens means mounted within the housing intermediate the first and second end portions 15 and 16 for magnifying an image from the endoscope 11 in order to provide a magnified image to the camera head 18. In other words, it is a single refracting unit for magnifying the image from the endoscope 11 and it is the sole refracting element for magnifying the image.

The lens 40 is retained within a cylindrically shaped focusing slide member or inner sleeve 41 adjacent a first window 42 (preferably glass) by a exteriorly threaded lens retaining ring 43 that screws into place within an interiorly threaded interior portion of the inner sleeve 41 (FIG. 3). Light passes along the optical axis through a first aperture 44, as indicated by the arrows in FIG. 3 that point to the right of the sheet of drawings. The light then passes through the lens 40, through a second aperture 45 that functions as an exit stop as well as a lens mounting member, and then through a second window 46 and out of the device 10, the windows helping to seal the lens 40.

Focusing is accomplished by moving the lens 40 relative to the proximal end 36 of the optical fiber 37. This is done by rotating the focusing ring 26 previously mentioned, the focusing ring 26 being illustrated in FIG. 6 in a position displaced ninety degrees from the position illustrated in FIG. 3.

A cylindrically shaped cam ring or outer sleeve 50 disposed between the housing 14 and the focusing ring 26 is coupled to the focusing ring 26 by a screw 51 that passes through the focusing ring 26, a hole 52 in the outer sleeve into a circumferentially extending groove 53 in the housing 14. This arrangement mounts both the focusing ring 26 and the outer sleeve 50 on the housing 14 so that when the user rotates the focusing ring 26, the outer sleeve 50 rotates with it.

However, neither move axially so that contaminants do not collect under the outer sleeve 50. Elastomeric O-ring sealing members 54 and 55 (FIG. 3) provide seals between the outer sleeve 50 and the housing 14 that further this purpose.

The outer sleeve 50 defines a helically extending groove 56 that provides a cam surface, and the housing defines a longitudinally extending groove 57 that provides a keyway. A screw 58 extends through the grooves 56 and 57, through the housing 14, and into the inner sleeve 41. As the user rotates the focusing ring 26 as depicted by an arrow 59A in FIG. 7, the screw 58 is cammed within the helically extending groove 56 so that the inner sleeve 41 moves axially as depicted by an arrow 59B in FIG. 7, with the screw 58 being keyed or guided along the groove 57 so that the inner sleeve 41 does not rotate. Rotating the focusing ring 26 in the opposite direction causes the inner sleeve 41 to move axially in the opposite direction.

In other words, as the user rotates the focusing ring 26, the lens 40 moves axially relative to the proximal end 36 of the optical fiber 37, and this enables the user to make fine focusing adjustments. This relieves the manufacturer from dimensional tolerances that might otherwise be required by compensating for dimensional variances in the system, and this arrangement may be said to serve as focusing means for enabling a user to adjust the distance of the lens 40 from the endoscope 11 for focusing purposes. In other words, it serves as means for causing the lens 40 to move axially as the focusing ring 26 is rotated.

The further enlarged view of FIG. 8 shows lens placement and an abbreviated ray diagram. Known optical design techniques are utilized to derive the distance from the proximal end 36 of the optical fiber 37 to the lens 40 that is designated by the letter "a" and the distance from the lens 40 to the forward surface 22 of the sensor chip 21 that is designated by the letter "b". For a thin lens having a focal length "f", these parameters have the known lens formula relationship:

$$1/a + 1/b = 1/f$$

In this regard, it is desired to magnify the image size to that it covers a substantial portion of the sensor chip and therefore the screen of the video monitor 24. It is also desirable to increase the light intensity on the screen. These objectives are realized in the direct coupling with one refracting element as described above.

However, magnification can not be increased indefinitely because the honeycomb of the optical fiber bundle eventually becomes discernible. If the cladding of each individual fiber of the optical fiber 36 is one micrometer, for example, then for a one-half inch sensor chip, such as the Panasonic sensor chip previously mentioned, the cell size is 8.82 μm (vertical) by 15.12 μm (horizontal) without looking into the detail configuration of the cell. One can conclude from this that the magnification of the optical fiber 36 should not be larger than 8× to avoid the honeycomb becoming discernible.

The above is one constraint. The other constraint is that the image provided by the optical fiber 36 should not be magnified bigger than the image site on the forward surface 22 of the sensor chip 21. In this regard, the Panasonic one-half inch sensor chip has image site dimensions of 4.32 mm (vertical) by 5.78 mm (horizontal). With these two constraints and the lens formula, the optimal magnification can be determined and the length of the coupler device calculated.

Considering now FIG. 9, there is shown an eyepiece 100 utilized in an imaging system according to the invention. It is generally similar in many respects to existing eyepieces, serving to interface the connector hub 12 to the eye of a user placed closely proximate the second end portion 116.

However, the eyepiece 100 incorporates a focusing ring 126 on a housing 114 that is similar to the focusing ring 26 and housing 14 of the device 10. In addition, a first end portion 115 of the eyepiece 100 is configured so that is compatible with the quick-release means of the device 10.

In other words, the first end portion 115 is dimensioned and arranged like the first end portion 15 of the device 10 so that the first end portion 115 of the eyepiece 100 can be snapped onto the connector hub 12. This enables interchangeable mounting of a selected one of the device 10 and the eyepiece 100 so that either the eyepiece or coupler device can be utilized at will by snapping off one and snapping on the other.

In addition, the eyepiece 100 may be configured to employ a single lens that is identical to the lens 40 of the device 10. When that is done, only one lens need be fabricated, with the resulting cost benefits of component standardization.

Thus, this invention provides a dedicated endoscope coupler device that includes a single refracting optical element or lens within a single mounting component or housing. It results in less expense and complexity. It simplifies mounting. It eliminates multiple focusing adjustments, and it increases light intensity while decreasing size.

In addition, a single refracting element exhibits less optical loss and it avoids problems associated with aberrations correction. Moreover, one lens mounted within one housing facilitates fabrication of different couplers having different magnification. In other words, the manufacturer can change physical dimensions of the housing instead of optical characteristics of the lens and thereby make use of the same type lens for different couplers.

Although an exemplary embodiment of the invention has been shown and described, many changes, modifications, and substitutions may be made by one having ordinary skill in the art without necessarily departing from the spirit and scope of this invention.

What is claimed is:

1. A coupler device for coupling an endoscope to a camera head, comprising:
   a housing defining a light path that extends along an optical axis between first and second end portions of the housing;
   first mounting means for attaching the first end portion of the housing to an endoscope and for enabling a user to attach the endoscope to the housing by advancing a proximal end of the endoscope axially relative to the first end portion of the housing without having to rotate the endoscope;
   second mounting means for attaching the second end portion of the housing to a camera head so that the light path extends toward the camera head; and
   lens means mounted within the housing intermediate the first and second end portions for magnifying an image from the endoscope in order to provide a magnified image to the camera head;
   the first mounting means including means for maintaining concentricity between a connector hub on the proximal end of the endoscope and the coupler device;
   the means for maintaining concentricity including the first end portion of the housing being dimensioned and arranged to receive a tip portion of the connector hub and at least one radially extending member mounted on the first end portion that is arranged to extend radially inwardly to engage a circumferentially extending groove in the tip portion of the connector hub when the tip portion is inserted into the first end portion of the coupler device.

2. A device as recited in claim 1, wherein:
   the first mounting means is configured to retain the first end portion of the housing adjacent the proximal end of an endoscope imaging fiber so that the proximal end of the endoscope imaging fiber faces into the housing along the light path.

3. A device as recited in claim 1, wherein the second mounting means includes:
   a connector hub attached to the endoscope; and
   quick-release means for enabling a user to attach the connector hub to and detach the connector hub from the first end portion of the housing by advancing the connector hub axially relative to the first end portion of the housing without having to rotate the connector hub.

4. A device as recited in claim 1, further comprising:
   antirotation means for preventing rotation of the first end portion relative to the connector hub.

5. A device as recited in claim 1, wherein the second mounting means includes:
   the second end portion of the housing having a threaded portion dimensioned and arranged to be screwed onto the camera head, the second end portion being configured for attachment to a conventional C mount.

6. A device as recited in claim 1, wherein:
   the lens means includes a single refracting optical element for magnifying the image from the endoscope that is the sole refracting optical element for magnifying the image.

7. A device as recited in claim 6, further comprising:
   focusing means for enabling a user to adjust the distance of the lens from the endoscope for focussing purposes.

8. A coupler device for coupling an endoscope to a camera head, comprising:
   a housing defining a light path that extends generally along an optical axis between first and second end portions of the housing;
   first mounting means for receiving a connector hub on a proximal end of an endoscope so that the first end portion of the housing is retained adjacent a proximal end of an endoscope imaging fiber in a position such that the proximal end of the endoscope imaging fiber faces into the housing along the light path and for enabling a user to attach the endoscope to the coupler device by advancing a proximal end of the endoscope axially relative to the first end portion of the coupler device without having to rotate the endoscope;
   second mounting means for mounting the second end portion of the housing on a camera head so that the light path extends toward the camera head; and
   lens means mounted within the housing intermediate the first and second end portions for magnifying an image from the endoscope in order to provide a magnified image to the camera head;
   the first mounting means including means for maintaining concentricity between a connector hub on the proximal end of the endoscope and the coupler device;
   the means for maintaining concentricity including the coupler device having a first end portion dimensioned and arranged to receive a tip portion of the connector hub and a plurality of radially extending members arranged to extend inwardly to engage a circumferentially extending groove in the tip portion of the connector hub when the tip portion is inserted into the first end portion of the coupler device.

9. An imaging system, comprising:
   an imaging endoscope;
   camera coupler means for coupling the endoscope directly to a camera head, the coupler means including a housing and the housing defining a light path that extends along an optical axis between first and second end portions of the housing;
   first mounting means for attaching the first end portion of the housing to the endoscope and for enabling a user to attach the endoscope to and detach the endoscope from the first end portion of the housing by advancing a proximal end of the endoscope axially relative to the first end portion of the housing without having to rotate the endoscope; and
   second mounting means for attaching the second end portion of the housing to a camera head so that the light path extends toward the camera head;
   the second mounting means including the second end portion of the housing having a threaded portion dimensioned and arranged to be screwed onto the camera head, which second end portion is configured for attachment to a conventional C mount.

10. An imaging system as recited in claim 9, further comprising:
    eyepiece means for interfacing the endoscope to a human eye, which eyepiece means is compatible with the quick-release means to enable interchangeable mounting on the endoscope of a selected one of the camera coupler means and the eyepiece means.

11. An imaging system as recited in claim 9, wherein the imaging endoscope includes:
a connector hub attached to the proximal end portion of the endoscope; and
a tip portion of the connector hub that is dimensioned and arranged to fit into the first end portion of the coupler device;
the tip portion defining a recess that is dimensioned and arranged to receive radially extending members attached to the first end portion for purposes of providing a quick-release attachment to the coupler device.

12. An imaging system as recited in claim 11, wherein:
the recess is in the form of a circumferentially extending groove in the tip portion.

13. An imaging system as recited in claim 11, wherein the connector hub includes:
antirotation means for preventing rotation of the connector hub relative to the coupler device.

14. An imaging system as recited in claim 13, wherein the antirotation means includes:
a circularly shaped flange portion of the connector hub that defines a plurality of spaced apart notches.

15. An imaging system, comprising:
an imaging endoscope having a proximal end portion and a connector hub attached to the proximal end portion;
a coupler device for coupling the endoscope to a camera head and an eyepiece device for interfacing the endoscope to an eye; and
quick-release means for enabling a user to attach the endoscope to a selected one of the coupler device and the eyepiece device by advancing a proximal end of the endoscope axially relative to a first end portion of the selected one without having to rotate the endoscope;
the quick-release means including means for maintaining concentricity between the connector hub and the selected one of the coupler device and the eyepiece device;
the means for maintaining concentricity including the coupler device having a first end portion, the eyepiece device having a first end portion, and the connector hub having a tip portion that is dimensioned and arranged to fit without the first end portion of the coupler device and the first end portion of the eyepiece device, a circumferentially extending groove in the tip portion, at least one radially extending member attached to the first end portion of the coupler device, and at least one radially extending member attached to the first end portion of the eyepiece device, which radially extending members are arranged to extend inwardly to engage the groove when the tip portion is inserted into the first end portion.

16. An imaging system as recited in claim 15, wherein each one of the radially extending members includes:
a screw extending through the first end portion of a respective one of the coupler device and the eyepiece device to a tip of the screw; and
a spring loaded ball arrangement attached to the tip of the screw.

17. An imaging system as recited in claim 15, wherein the coupler device includes:
a housing defining a light path that extends along an optical axis between first and second end portions of the housing;
first mounting means for attaching the first end portion of the housing to an endoscope;
second mounting means for attaching the second end portion of the housing to a camera head so that the light path extends toward the camera head; and
lens means mounted within the housing intermediate the first and second end portions for magnifying an image from the endoscope in order to provide a magnified image to the camera head.

18. An imaging system as recited in claim 17, wherein the first mounting means includes:
means for retaining the first end portion of the housing adjacent the proximal end of an endoscope imaging fiber so that the proximal end of the endoscope imaging fiber faces into the housing along the light path.

19. An imaging system as recited in claim 18, further comprising:
antirotation means for preventing rotation of the first end portion relative to the connector hub.

20. An imaging system as recited in claim 17, wherein the second mounting means includes:
the second end portion of the housing having a threaded portion dimensioned and arranged to be screwed onto the camera head, which second end portion is configured for attachment to a conventional C mount.

21. An imaging system as recited in claim 17, further comprising:
focusing means for enabling a user to adjust the distance of the lens from the endoscope for focusing purposes.

22. An imaging system as recited in claim 21, wherein the focusing means includes:
a ring circumscribing the housing, which ring is mounted on the housing to enable a user to rotate the ring about the optical axis; and
means for causing the lens to move axially as the ring is rotated.

23. An imaging system as recited in claim 15, wherein the coupler device includes:
a housing of unitary construction defining a light path that extends generally along an optical axis between first and second end portions of the housing;
first mounting means for receiving the connector hub so that the first end portion of the housing is retained adjacent the proximal end of an imaging fiber of the imaging endoscope in a position such that the proximal end of the imaging fiber faces into the housing along the light path;
second mounting means for mounting the second end portion of the housing on a camera head so that the light path extends toward the camera head; and
lens means mounted within the housing intermediate the first and second end portions for magnifying an image from the endoscope in order to provide a magnified image to the camera head.

24. An optical interfacing device for use with an endoscope of the type which has a proximal end, a connector hub connected to the endoscope adjacent the proximal end, a circumferentially extending groove in the connector hub, and means for transmitting an image proximally, said optical interfacing device comprising:

a housing having first and second end portions and a passage extending between the first and second end portions, said housing defining a light path that extends along an optical axis through the passage;

said passage opening at said first end portion to receive the connector hub;

a radially movable element biased radially inwardly into said passage adjacent said first end portion and being receivable in the groove of the connector hub to releasably attach the endoscope to the housing; and a lens mounted on said housing within said passage and along the optical axis.

25. An optical interfacing device as defined in claim 24 including means on the housing for interfacing the housing to an eye of a user when the eye of the user is placed closely proximate the second end portion.

26. An optical interfacing device as defined in claim 25 including mounting means for attaching the second end portion of the housing to a camera head so that the light path extends toward the camera head.

27. An imaging system, comprising:

an endoscope having a proximal end portion and a connector hub attached to the proximal end portion;

an eyepiece device for interfacing the endoscope to an eye; and quick-release means for enablig a user to attach the endoscope to the eyepiece device by advancing a proximal end of the endoscope axially relative to the eyepiece without having to rotate the endoscope;

the eyepiece device including a housing having first and second end portions and a passage extending between the first and second end portions, said housing defining a light path that extends along an optical axis through the passage;

said passage opening at said first end portion to receive the connector hub; and the quick-release means including a radially movable element mounted on the housing that is biased radially inwardly into said passage adjacent said first end portion and being receivable in the groove of the connector hub to releasably attach the endoscope to the housing.

28. An imaging system as recited in claim 27, wherein the eyepiece device includes:

a lens mounted on said housing within said passage and along the optical axis.

29. An imaging system as recited in claim 27, further comprising:

a coupler device for coupling the endoscope to a camera head, which coupler device includes quick-release means for enabling a user to attach the endoscope to the coupler device by advancing the proximal end portion of the endoscope axially relative to the coupler device without having to rotate the endoscope.

* * * * *

UNITED STATES PATENT AND TRADEMARK OFFICE
CERTIFICATE OF CORRECTION

PATENT NO. : 4,844,071

DATED : July 4, 1989

INVENTOR(S) : Chingfa Chen et al

It is certified that error appears in the above-identified patent and that said Letters Patent is hereby corrected as shown below:

Column 3, line 23 change "This" to -- The --.

Column 4, line 13 change "This" to -- That --.

Column 4, line 61 change "seprate" to -- separate --.

Column 5, line 45, change "entending" to -- extending --.

Column 5, line 46 change "of" to -- or --.

Column 6, line 19 change "housiing" to -- housing --.

Column 7, line 68 change "to that" to -- so that --.

Column 10, line 2 change "focussing" to -- focusing --.

Column 11, line 49 change "without" to -- within --.

Column 13, line 28 change "enablig" to -- enabling --.

Signed and Sealed this

Third Day of July, 1990

Attest:

HARRY F. MANBECK, JR.

*Attesting Officer*     *Commissioner of Patents and Trademarks*